United States Patent [19]
Villa et al.

[11] Patent Number: 6,001,344
[45] Date of Patent: Dec. 14, 1999

[54] LIQUID CLEANSING COMPOSITIONS COMPRISING XANTHAN GUM AND CROSS-LINKED POLYACRYLIC ACID POLYMERS FOR ENHANCED SUSPENSION OF LARGE DROPLET OILS

[75] Inventors: Virgilio Villa, Bergenfield; Richard Kolodziej, Cliffside Park; May Shana'a, Fort Lee, all of N.J.

[73] Assignee: Lever Brothers Company, Division of Conopco, Inc., New York, N.Y.

[21] Appl. No.: 08/610,565

[22] Filed: Mar. 6, 1996

[51] Int. Cl.$^6$ ....................................................... A61K 7/50
[52] U.S. Cl. ...................... 424/78.02; 510/130; 510/158; 510/159; 514/944; 514/970; 516/107
[58] Field of Search ................... 424/78.02, 57; 510/119, 121, 130, 135, 137, 158, 159; 514/937, 944, 970; 516/98, 99, 100, 104, 105, 107

[56] References Cited

U.S. PATENT DOCUMENTS

| | | | |
|---|---|---|---|
| 3,663,284 | 5/1972 | Stancioff et al. | 106/447 |
| 4,032,669 | 6/1977 | Peters et al. | 426/573 |
| 4,105,461 | 8/1978 | Racciato | 106/205.01 |
| 4,143,175 | 3/1979 | Whelan et al. | 426/582 |
| 4,145,454 | 3/1979 | Dea et al. | 426/565 |
| 4,364,837 | 12/1982 | Pader | 252/173 |
| 4,491,539 | 1/1985 | Hoskins et al. | 252/541 |
| 4,591,610 | 5/1986 | Grollier | 524/55 |
| 4,678,606 | 7/1987 | Akhter et al. | 252/542 |
| 4,788,006 | 11/1988 | Bolich, Jr. et al. | 252/550 |
| 4,927,563 | 5/1990 | McCall | 252/551 |
| 5,085,857 | 2/1992 | Reid et al. | 424/70.12 |
| 5,260,051 | 11/1993 | Cho | 424/57 |
| 5,344,643 | 9/1994 | Thiel et al. | 424/70.11 |
| 5,368,843 | 11/1994 | Rennie . | |
| 5,409,695 | 4/1995 | Abrutyn et al. | 424/70.12 |
| 5,447,652 | 9/1995 | Nozaki et al. | 252/174.16 |
| 5,585,104 | 12/1996 | Ha et al. | 424/401 |
| 5,607,980 | 3/1997 | McAtee et al. | 514/476 |
| 5,929,019 | 7/1999 | Puvvada et al. | 510/406 |

*Primary Examiner*—Robert H. Harrison

[57] ABSTRACT

The present invention relates to a novel structuring system comprising both xanthan gum and cross-linked polyacrylic acid polymer which combination unexpectedly has been found to provide enhanced stability for large size benefit agent droplets in an amphoteric/anionic surfactant system relative to use of either structurant alone.

8 Claims, No Drawings

LIQUID CLEANSING COMPOSITIONS COMPRISING XANTHAN GUM AND CROSS-LINKED POLYACRYLIC ACID POLYMERS FOR ENHANCED SUSPENSION OF LARGE DROPLET OILS

FIELD OF THE INVENTION

The present invention relates to liquid shower gel compositions comprising oils/emollients as benefit agents. In particular, the application relates to combination of both xanthan gum and cross-linked polyacrylic acid polymers which unexpectedly has been found capable of stably suspending large size oil/emollient droplets better than either one alone.

BACKGROUND

Liquid cleanser compositions providing some kind of benefit agent are known in the art. Thus, for example, the use of silicones, oils and other emollients in liquid compositions for providing skin care benefit is known.

One method of enhancing the delivery of the benefit agent (e.g., vegetable oil, silicone) to the skin or hair, for example, is through the use of cationic hydrophilic polymers such as Polymer JR® from Americhol or Jagua® from Rhone Poulenc (see WO 94/03152). In this reference generally small sized silicone particles are uniformly distributed throughout the liquid cleanser.

Another way of enhancing delivery of benefit agent is utilizing larger size benefit agent particles. To suspend such particles without causing separation of the particles or oil droplets (e.g., flocculation, coalescence, creaming or breaking), however, is not an easy task.

One way of suspending larger size particles is through the use of thickeners such as xanthan gum. Xanthan gum thickeners are taught, for example, in U.S. Pat. No. 4,364,837 to Pader (see column 22, Table II, example 16); and in U.S. Pat. No. 4,788,006 to Bolich Jr.

U.S. Pat. No. 4,541,610 to Grollier (L'Oreal) teaches thickened or gelled hair conditioning compositions which use xanthan gum as thickener. All the examples appear to exemplify only a cationic surfactant as principal surfactant and there appears to be no teaching of an oil or emollient, let alone a disclosure of particle size.

Several patents also disclose the use of a cross-linked polyacrylic type polymer with silicone. U.S. Pat. No. 5,085,857 to Reid et al., for example, teaches in example 1 a Carbopol® in combination with silicone oil. There is no teaching of xanthan gum, however, and the silicone oil is an emulsion, i.e., not large sized silicone droplets (typically median particle sizes of emulsions are about 0.3 to 0.5 microns).

U.S. Pat. No. 5,344,643 to Thiel teaches shampoo compositions comprising an oily conditioning agent, (e.g., silicone), a carboxyvinyl polymer, a cationic conditioning agent and water. There is no teaching of xanthan gum.

U.S. Pat. No. 5,409,695 to Abrutyn et al. teaches a method of depositing silicone by entrapping silicone in a nontoxic hydrophobic macroporous highly x-linked polymer. There is no xanthan gum.

SUMMARY OF THE INVENTION

Suddenly and unexpectedly, applicants have found that when xanthan gum and cross-linked polyacrylic acid polymer saturated compounds (e.g., polyacrylate or polymethacrylate) are used in the specified surfactant system of the invention, they stably suspend large benefit agent particles. By contrast, when xanthan gum or cross-linked polyacrylic acid polymer is used alone, the benefit agent cannot be suspended without separation.

Specifically, in one embodiment of the invention, the invention comprises a liquid cleansing composition comprising:

(1) 5% to 50% by wt. of a surfactant system comprising
  (a) anionic surfactant or mixture of anionic surfactants; and
  (b) an amphoteric and/or zwitterionic surfactant or mixture thereof;

(2) 0.1% to 20% by wt., preferably 0.5 to 15% by wt., most preferably 1% to 12% by wt. of a benefit agent of defined particle size (e.g, silicone oil);

(3) 0.01 to 5.0%, preferably 0.05 to 2.0%, most preferably 0.1 to 1.5% by wt. xanthan gum; and (4) 0.01 to 5.0%, preferably 0.05 to 2.0%, most preferably 0.1 to 1.0% by weight of a cross-linked polyacrylic acid polymer (e.g., polyacrylate or polymethacrylate).

In a second embodiment of the invention, the invention comprises a method for stably suspending large size benefit agent particles (i.e., 1 to 500 microns, preferably 2 to 200 microns, more preferably 2 to 100 microns) using the compositions of the invention.

DETAILED SUMMARY OF THE INVENTION

The present invention relates to a liquid detergent composition comprising a structurant system capable of suspending large size (e.g., 1 to 500 microns) benefit agent particles. The structurant system comprises a combination of xanthan gum and cross-linked polyacrylic acid polymers such as cross-linked polyacrylates or methacrylates.

Surfactants

The surfactant system of the subject invention comprises 5 to 50% by weight, preferably 10 to 40% by wt. of the composition and comprises:

(a) one or more anionic surfactants;
(b) amphoteric and/or zwitterionic surfactant; and
(c) optional nonionic surfactant The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 4; and M is a solubilizing cation such as sodium, potassium, magnesium, ammonium or substituted ammonium, magnesium, ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$R^4O_2CCH_2CH(SO_3M)CO_2M$;

amido-MEA sulfosuccinates of the formula $R^4CONHCH_2CH_2O_2CCH_2CH(SO_3M)CO_2M$ wherein $R^4$ ranges from $C_8$–$C_{22}$ alkyl and M is a solubilizing cation;

amido-MIPA sulfosuccinates of formula $RCONH(CH_2)CH(CH_3)(SO_3M)CO_2M$ where M is as defined above.

Also included are the alkoxylated citrate sulfosuccinates; and alkoxylated sulfosuccinates such as the following:

$$R-O-(CH_2CH_2O)_n\overset{O}{\underset{\|}{C}}CH_2CH(SO_3M)CO_2M$$

where n=1 to 20; and M is as defined above.

Sarcosinates are generally indicated by the formula $RCON(CH_3)CH_2CO_2M$ wherein R ranges from $C_8$ to $C_{20}$ alkyl and M is a solubilizing cation.

Taurates are generally identified by formula $R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$R-(CH_2CH_2O)_nCO_2M$ or $$R-O-(CH_2CH_2O)_{\overline{n}}-CH_2\overset{O}{\underset{\|}{C}}-O^-M^+$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application. This compound has the general formula:

$$R\overset{O}{\underset{\|}{C}}-O-\overset{X}{\underset{|}{C}}H-CH_2-(O\overset{Y}{\underset{|}{C}}H-CH_2)_m-SO^-_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In general the anionic component will comprise from about 1 to 25% by weight of the composition, preferably 2 to 20%, most preferably 5 to 15% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2-\overset{(R^3)_x}{\underset{|}{Y^{(+)}}}-CH_2-R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1-\!\!\left[\!\!\begin{array}{c}O\\\|\\C\end{array}\!\!\right]\!\!-NH(CH_2)_n\!\!\left.\right]_{\overline{m}}\!\!\overset{R^2}{\underset{R^3}{\overset{|}{N^+}}}\!\!-X-Y$$

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is $-CO_2-$ or $-SO_3-$ Suitable amphoteric detergents within the above general formula include simple betaines of formula:

$$R^1-\underset{R^3}{\overset{R^2}{\overset{|}{\underset{|}{N^+}}}}-CH_2CO_2^-$$

and amido betaines of formula:

$$R^1-CONH(CH_2)_{\overline{m}}-\underset{R^3}{\overset{R^2}{\overset{|}{\underset{|}{N^+}}}}-CH_2CO_2^-$$

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula $$R^1-\underset{R^3}{\overset{R^2}{\overset{|}{\underset{|}{N^+}}}}-(CH_2)_3SO_3^- \quad \text{or}$$

$$R^1-CONH(CH_2)_{\overline{m}}-\underset{R^3}{\overset{R^2}{\overset{|}{\underset{|}{N^+}}}}-(CH_2)_3SO_3^-$$

where m is 2 or 3, or variants of these in which $-(CH_2)_3SO_3^-$ is replaced by $$-CH_2\overset{OH}{\underset{|}{C}}HCH_2SO_3^-$$

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic generally comprises 0.1 to 20% by weight, preferably 5% to 15% of the composition.

In addition to one or more anionic and amphoteric and/or zwitterionic, the surfactant system may optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic comprises 0 to 10% by wt. of the composition.

Oil/Emollient

One of the principal benefits of the invention is the ability to suspend large particle size oil/emollient particles in an isotropic phase composition.

Various classes of oils are set forth below.

Vegetable oils: Arachis oil, castor oil, cocoa butter, coconut oil, corn oil, cotton seed oil, jojoba oil, olive oil, palm kernel oil, safflower oil, rapeseed oil, sunflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, propylene glycol isostearate, glycerol trioctanoate, glyceryl tricaprylate/tricaprate, isostearyl isostearate, pentaerythrityl tetraisostearate.

Animal Fats: Acytylated lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include mineral oil, petrolatum, beeswax, polyisobutene, silicone oil such as dimethyl polysiloxane, lauryl and myristyl lactate.

The emollient/oil is generally used in an amount from about 1 to 20%, preferably 1 to 15% by wt. of the composition. Generally, it should comprise no more than 20% of the composition.

The particles of the invention generally have a size of 1 to 500, preferably 2 to 200, most preferably 2 to 100 microns.

An especially preferred oil is silicone oil, in particular, dimethicone having viscosity of 60,000 centistokes.

Xanthan Gum

The xanthan gums used according to the present invention are known per se and are polysaccharides which can be synthesized by fermentation of certain sugars by microorganisms, such as the bacterium Xanthomonas campestris.

These gums generally have a molecular weight of from 1 million to 50 million and a viscosity of from 850 to 1,600 cps for an aqueous composition containing 1% of xanthan gum (gum was present in a 1% KCl solution and was measured on a viscometer of the Brookfield LV type, at 60 revolutions/minute using Spindle No. 3).

Gums which are more particularly preferred according to the invention are commercial products, such as Keltrol, marketed by Kelco, Rhodopol 23 C, marketed by Rhone-Poulenc, Actigum CX 9, marketed by Ceca, and Deuteron XG, marketed by Schoner.

The xanthan gum generally will comprise from 0.01 to 5.0% by wt. of the cleanser composition. Preferably, the gum should comprise 0.1 to 1.5% by wt. of the composition.

Cross-Linked Polyacrylic Acid Polymer

The second component of the structuring system (in addition to xanthan gum) is the cross-linked polyacrylic acid polymer. Preferably, this is a cross-linked polyacrylate or polymethacrylate compound. Examples of such compounds include Carbopol® and Pemulen® from B. F. Goodrich; and Acritame® from RITA.

The cross-linked structurant generally comprises 0.01 to 5.0% by wt., preferably 0.05 to 2.0 by wt. of the liquid composition.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 5-chloro-2-(2,4-Dichlorophenoxy) phenol phenol (DP300); preservatives such as 1,3-Dimethylol-5,5-dimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.005% or higher if appropriate.

Cationic conditioners which may be used include Quatrisoft LM-200 Polyquaternium-24, Merquat Plus 3330 - Polyquaternium 39, Jagua® type conditioners (including guar gum), polymethacrylamido propyl chloride, polyquaternium 37 and polyquatemium 10.

Polyethylene glycols which may be used include:

| Polyox | WSR-205 | PEG 14M, |
| Polyox | WSR-N-60K | PEG 45M, or |
| Polyox | WSR-N-750 | PEG 7M. |

Thickeners which may be used include Amerchol Polymer HM 1500 (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt); ammonium sulfate, and sodium chloride.

Another optional ingredient which may be added are the deflocculating polymers such as are taught in U.S. Pat. No. 5,147,576 to Montague, hereby incorporated by reference.

Another ingredient which may be included are exfoliants such as polyoxyethylene beads, ground walnut shells and ground apricot seeds.

In a second embodiment of the invention, the invention relates to a method of stabilizing large size benefit droplets in specific surfactant systems using the combination of xanthan gum and cross-linked polyacrylic acid polymers as a structuring system.

EXAMPLES

Protocol

Assessment of Stability was done by one of the 4 following mechanisms.

(1) Visual assessment based on 2-phase separation;

(2) Microscopy—determination of presence of benefit agent droplets at different points (i.e., top and bottom) of sample;

(3) Particle size distribution—laser scattering based particle size/particle size distribution at different sampling points; and (4) Determination of theoretical creaming rate of the droplets.

Product stability for compositions of the invention (using most of the techniques described above) was assessed using accelerated conditions (i.e., 1 week minimum at 125° F.).

Using the accelerated conditions noted above, compositions 1–13 were prepared and assessed as follows:

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Cocoamidopropyl Betaine | 10 | 10 | 10 | 10 | 10 | 10 | 10 | 10 | 10 | 10 | 10 | 10 | 10 | 8 | 8 |
| Sodium Cocyl Isethionate | 5 | 5 | 5 | 6 | 5 | 5 | 5 | 5 | 5 | 5 | 5 | 5 | 5 | 4 | 4 |

-continued

|  | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Sodium Laureth Sulfate | 5 | 5 | 5 | 5 | 5 | 5 | 5 | 5 | 5 | 5 | 5 | 5 | 5 | 3 | 3 |
| Dimethicone (60,000 cst) | 5 | 5 | 5 | 6 | 5 | 5 | 5 | 5 | 5 | 5 | 5 | 5 | 5 | 5 | 5 |
| Carbopol ETD 2020[1] | 0.2 | 0.4 | 0.6 | 0.8 | — | — | 0.4 | 0.4 | — | — | 0.4 | 0.4 | 0.4 | 0.4 | 0.4 |
| Xanthan Gum | — | — | — | — | — | — | — | — | 0.1 | 0.2 | 0.05 | 0.1 | 0.2 | 0.2 | 0.3 |
| Polysurf 67[2] | — | — | — | — | 0.1 | 0.2 | 0.1 | 0.2 | — | — | — | — | — | — | — |
| Opacifier/Colorant | 0.6 | 0.6 | 0.6 | 0.6 | 0.6 | 0.6 | 0.6 | 0.6 | 0.6 | 0.6 | 0.6 | 0.6 | 0.6 | 0.6 | 0.6 |
| Perfume/Preservative | 1.2 | 1.2 | 1.2 | 1.2 | 1.2 | 1.2 | 1.2 | 1.2 | 1.2 | 1.2 | 1.2 | 1.2 | 1.2 | 1.2 | 1.2 |
| Diluent, Water to | 100 | 100 | 100 | 100 | 100 | 100 | 100 | 100 | 100 | 100 | 100 | 100 | 100 | 100 | 100 |
| Produce Separation[3] | V | V | V | V | V | V | V | V | V | V | NV | NV | NV | NV | NV |

[1]Acrylate/C10–C30 Alkyl Acrylate Copolymer
[2]Cetyl Hydroxyethyl Cellulose
[3]V (Visible separation), NV (No Visible Sign of Instability); Assessments Made After 1 Week at 125° F.

Example 1

As seen from Table 1, benefit agent (e.g., silicone) was suspended in the following structurant systems (1) where Carbopol (0.2% to 0.8%) was sole structurant (Examples 1–4); (2) where Polysurf 67, cetyl hydroxyethylcellulose (0.1% to 0.2%), was sole structurant (Examples 5 and 6); (3) where Ketrol RD, xanthan gum (0.1 to 0.2%) was sole structurant (Example 9 and 10); (4) where Carbopol and xanthan together were used together as structurants (Examples 11–13) and (5) where Carbopol and Polysurf 67 together were used as structurants (Examples 7 and 8).

It was clearly noted by visual assessment using the protocol noted above that any of the three alone (Groups (1)–(3)) or Carbopol plus Polysulf (Group (5)) were unstable. By contrast, Carbopol plus xanthan (Group (4)) (Examples 11–13) were visually stable (i.e., no visible sign of instability over accelerated conditions).

Thus, there was clearly an unexpected enhancement in stability when these two specific structurants were used together.

It should be noted that the same results were observed in lower surfactant systems (Example 14 and 15).

Example 2

|  | % (by weight) |
|---|---|
| Cocamidopropyl Betaine | 10.0 |
| Sodium Cocyl Isethionate | 5.0 |
| Sodium Laureth Sulfate | 5.0 |
| Dimethicone (60,000 cst) | 5.0 |
| Carbopol ETD 20201 | 0.4 |
| Xanthan Gum | 0.2 |
| Opacifier/Colorant | 0.6 |
| Perfume/Preservative | 1.2 |
| Diluent, Water to | 100.0 |

The above composition was prepared according to the procedure described below comprising about 20% surfactants, 0.4% Carbopol, 0.2% Xanthan Gum and 5% Silicone.

Using microscopy technique (there was no visual separation), sample from top and bottom layers were compared at 100× magnification and it was found that oil droplets were uniformly distributed. Applicants then took a quantative determination of oil droplet size distribution from both top and bottom layers after 3 weeks at 125° F., using the Mastersizer (laser scattering based particle analyzer) and the following results were noted:

|  | Top Layer | Bottom Layer |
|---|---|---|
| Mean Particle Size ($\mu$m)[1] | 18.87 | 25.24 |
| Mode ($\mu$m) | 21.89 | 22.08 |
| $D_{90}$ (90th Percentile)[2] | 31.89 | 34.81 |

[1]mean particle size over the volume distribution (Herdan or Brouckere diameter).
[2]90% of particles are equal or less than this value.

Noting that particle sizes in both layers are extremely close in size after 3 weeks at 125° F., it is clear that the product is stable.

The procedure by which Example 2 composition was made is as follows:

1. Charge water into the mixing vessel.
2. Add Sodium Cocoyl Isethionate into the vessel and heat the mixture to 160–170° F.
3. Add Sodium Laureth Sulfate\pearlizer blend and continue mixing.
4. Add Carbopol ETD202 premix into the mix and neutralize to pH=5.5–6.5.
5. Add opacifier.
6. Add Dimethicone 60,000 cst and mix for 20 minutes.
7. Add Xanthan gum submix.
8. Add diluent to reduce viscosity.
9. Add Cocamidopropyl betaine and continue mixing.
10. Add preservative and perfume.
11. At 95° F., check product viscosity, appearance, consistency and add diluent as needed in order to attain acceptable rheology.

Example 3

Example 3 composition was similar to Example 2 but was subjected to lower shear rate.

In another example using the same chemical composition as in Example 2, except that silicone oil is subject to lower shear rate, the result of visual and microscopic determination of product separation revealed no signs of instability. This was confirmed when particle size measurements was taken on sample that was stored after 7 weeks at 125° F. as shown below:

|                               | Top Layer | Bottom Layer |
|-------------------------------|-----------|--------------|
| Mean Particle Size ($\mu$m)[1] | 41.74     | 45.01        |
| Mode ($\mu$m)                 | 41.32     | 40.93        |
| $D_{90}$ (90th Percentile)[2] | 61.44     | 62.85        |

Again, closeness of particle size in top and bottom layers clearly shows that the product is stable.

Example 4

Another method of showing stability is by showing rate of creaming is very low. This rate is measured by Stoke equations;

$$V_s = \frac{2r^2 g(\delta - \rho)}{9\eta_o}$$

where:

r=droplet radius, m
g=acceleration due to gravity, 9.807 m/sec$^2$
$\delta$=density of suspending liquid, kg/m$^3$
$\rho$=density of the droplet, kg/m$^3$
$\eta_o$=viscosity at zero shear rate, Pa s
$V_s$=creaming velocity, m/sec Using this equation, the following numbers were determined for surfactant systems comprising 20% actives.

| Surfactant, %                              | 20       |
|--------------------------------------------|----------|
| Xanthan gum level, %                       | 0.2      |
| r, radius @ 90%-tile (m)                   | 0.00003  |
| g, gravity constant (m/sec$^2$)            | 9.807    |
| $\delta$, density of suspending medium (kg/m$^3$) | 1030 |
| $\rho$, density of droplet (kg/m$^3$)      | 970      |
| $\eta_o$, viscosity at zero shear rate (Pa s)* | 2,560 |
| $V_s$, creaming rate (mm/year)             | 0.36     |

*Number was obtained by extrapolating from plot of shear rate versus viscosity for very low shear rates.

Using these numbers, the creaming rate at 25° C. was determined to be <1.0 mm/year. This again clearly shows the unexpected stability using the xanthan gum/cross-linked polyacrylate polymer structuring system of the invention.

Example 5

The following composition with 15% active was prepared.

|                              | % (by weight) |
|------------------------------|---------------|
| Cocamidopropyl Betaine       | 8.0           |
| Sodium Cocyl Isethionate     | 5.0           |
| Sodium Laureth Sulfate       | 2.0           |
| Dimethicone (60,000 cst)     | 5.0           |
| Carbopol ETD 20201           | 0.4           |
| Xanthan Gum                  | 0.3           |
| Opacifier/Colorant           | 0.6           |
| Perfume/Preservative         | 1.2           |
| Diluent, Water to            | 100.0         |

The chemical composition above was prepared and analyzed for particle size and results are as follows:

|                               | Top Layer | Bottom Layer |
|-------------------------------|-----------|--------------|
| Mean Particle Size ($\mu$m)[1] | 46.79    | 51.14        |
| Mode ($\mu$m)                 | 48.81     | 49.36        |
| $D_{90}$ (90th Percentile)[2] | 71.88     | 78.15        |

In this example, it can be seen that larger size droplets are found in both top and bottom layers even though less active (i.e., 15% versus 20%) is used.

This example not only confirms that at higher levels of xanthan (0.3% versus 0.2%), there is far less tendency to separate, but it also shows that at lower surfactant levels, the droplet size tends to be larger. While not wishing to be bound by theory, this may be because, at lower surfactant level, less shearing is required and the particles are thus not so readily broken up.

Theoretical prediction of creaming rate, using the Stoke's equation, is summarized below:

| Surfactant, %                              | 15        |
|--------------------------------------------|-----------|
| Xanthan gum level, %                       | 0.3       |
| r, radius @ 90%-tile (m)                   | 0.000082  |
| g, gravity constant (m/sec$^2$)            | 9.807     |
| $\delta$, density of suspending medium (kg/m$^3$) | 1030 |
| $\rho$, density of droplet (kg/m$^3$)      | 970       |
| $\eta_o$, viscosity at zero shear rate (Pa s)* | 2,440 |
| $V_s$, creaming rate (mm/year)             | 0.76      |

Again, creaming rates confirm stability of the composition.

We claim:

1. Liquid shower gel composition comprising:
    (a) 5% to 50% by wt. of a surfactant system comprising:
        (i) anionic surfactant or mixture of anionic surfactants; and
        (ii) an amphoteric or zwitterionic surfactant or mixtures thereof;
    (b) 0.1% to 20% by wt. of an oil or emollient skin care benefit agent particles having a mean particle size over volume distribution of 1 to 500 microns, wherein measurement for volume distribution is made using Herdan or DeBrouckere diameter;
    (c) 0.01 to 5.0% by wt. of a xanthan gum; and
    (d) 0.01 to 5.0% by wt. of a cross-linked polyacrylic acid polymer; wherein said composition is stable at least one week after exposure to temperature of 125° F.

2. A composition according to claim 1, comprising 10% to 40% surfactant system.

3. A composition according to claim 1, wherein particle size of oil or emollient is 2 to 200 microns.

4. A composition according to claim 1, comprising 0.5 to 15% oil or emollient.

5. A composition according to claim 1, wherein the oil or emollient is silicone.

6. A composition according to claim 1, comprising 0.05 to 2.0% xanthan gum.

7. A composition according to claim 1, comprising 0.05 to 2.0 cross-linked polyacrylic acid polymer.

8. A composition according to claim 7, wherein the polymer is polyacrylate or polymethacrylate.

* * * * *